United States Patent [19]
Couetil

[11] Patent Number: 5,078,738
[45] Date of Patent: Jan. 7, 1992

[54] ARTIFICIAL CARDIAC VALVE

[75] Inventor: Jean-Paul Couetil, Paris, France

[73] Assignee: E.R.A.C.C. Etudes, Recherches et Applications en Chirurgie Cardiaque, Paris, France

[21] Appl. No.: 487,955
[22] PCT Filed: Nov. 14, 1988
[86] PCT No.: PCT/FR88/00558
  § 371 Date: Jul. 12, 1990
  § 102(e) Date: Jul. 12, 1990
[87] PCT Pub. No.: WO89/04154
  PCT Pub. Date: May 18, 1989

[30] Foreign Application Priority Data
Nov. 13, 1987 [FR] France ................................ 87 15728

[51] Int. Cl.⁵ .............................................. A61F 2/24
[52] U.S. Cl. .................................................... 623/2
[58] Field of Search .......................................... 623/2

[56] References Cited
U.S. PATENT DOCUMENTS
4,328,592  5/1982  Klawitter .................................. 623/2
4,443,894  4/1984  Klawitter .................................. 623/2

FOREIGN PATENT DOCUMENTS
0211576  2/1987  European Pat. Off. ................. 623/2
0438415  8/1974  U.S.S.R. ................................... 623/2
8900033  1/1989  World Int. Prop. O. ............... 623/2

Primary Examiner—Randy C. Shay
Attorney, Agent, or Firm—Sughrue, Mion, Zinn, Macpeak and Seas

[57] ABSTRACT

An artificial cardiac valve made of biocompatible material comprises an annular valve body and a flap pivotally lodged inside the valve body and possessing linking elements for cooperating with guiding and restraining means provided on an internal side wall of the annular valve body. The flap consists of a disc folded along an axis XX' parallel to one of its diameters through an angle between 0 and 30 degrees in such a way that opening of the valve is effected in two consecutive phases. The first phase corresponds to a rotation of the flap about the contact and hinging point A between a rear part of the flap and a lower edge of the side wall of the valve body until said linking elements abut against the guiding and restraining means. The second phase corresponds to a rotation of about an axis ZZ' parallel to the axis XX' until the rear part of the flap is parallel to the axis YY' of the annular body.

8 Claims, 4 Drawing Sheets

ARTIFICIAL CARDIAC VALVE

BACKGROUND OF THE INVENTION

The present invention relates to an artificial cardiac valve.

Numerous artificial cardiac valves employing flap valve devices of the ball, disc or flap type in the form of a hemi-disc, already exist.

This is the case, for example, of the valves described in Patent Applications EP 0 176 337 (CARBOMEDICS INC.), EP 0 023 797 (HEMEX INC.), EP 0 039 217 (MITRAL MEDICAL INTERNATIONAL, INC. and EP 0 050 971 (HEMEX INC.).

Furthermore, GB 2 084 299 (HEMEX INC.) describes a cardiac valve comprising an annular element and a flap pivotally lodged inside said element as well as linking elements adapted to cooperate with guiding and restraining means provided on the internal lateral wall of the annular element.

These documents describe in particular valves of the type comprising a flap with single pivoting disc. The disc in question pivots by means of hinges in the form of protuberances disposed on the inner wall of the body of the valve and which, due to their configurations and arrangements, are capable of provoking phenomena of thrombosis.

Furthermore, these valves are in a position of complete opening only when the flap has pivoted through a certain angle which is always less than 90° about an axis of rotation which merges with its diameter. In fact, the limited angle of 90° does not allow passive closure of the valve. Consequently, in the position of opening, half of the disc constituting the flap is engaged in the aorta, which may raise problems of flow and/or space requirements.

Moreover, it is observed that these valves tend to oscillate due to the great distance between the axis of rotation and the most remote end of the flap.

SUMMARY OF THE INVENTION

The present invention enables these drawbacks to be overcome for the first time and in satisfactory manner, by proposing an artificial cardiac valve made of biocompatible material, of the type comprising:

an annular element of axis YY, a flap pivotally lodged inside said element and presenting linking elements adapted to cooperate with guiding and restraining means provided on the internal side wall of the annular element, characterized in that said flap is constituted by a disc folded along a line XX' parallel to one of its diameters so as to present a rear part and a front part located on either side of the line XX', the rear and front parts forming therebetween an angle greater than 150°, with the result that the opening of the valve is effected in two consecutive phases, the first phase corresponding to a rotation of the flap about the contact and hinging point A of the rear part of the flap with the lower edge of the side wall of said element until said linking elements abut in the guiding and restraining means, and the second phase corresponding to a rotation about an axis ZZ' parallel to axis XX' until the rear part of the flap is parallel to axis YY' of the element.

The cardiac valve of the invention is also characterized in that said guiding and restraining means are constituted by two symmetrical lateral slideways made in the mass of the element and in which the linking elements of the flap are movably engaged.

These slideways may be constituted by an arc of circle of centre A and of radius equal to the rear part of the flap, or by hollows comprising, over at least a part of their periphery, straight flanks forming stops.

The linking elements are provided laterally and symmetrically on axis ZZ' of the flap and are preferably constituted by two pivots or two ears.

The cardiac valve of the invention therefore presents in position of opening a so-called rear part parallel to the axis of the element, which is not produced with the disc valves of the prior art.

On the other hand, the two orifices existing during opening between the flap and the inner wall of the element and constituting the passageways for the flow of blood are of substantially equal dimensions.

In addition, the lateral internal wall of the element of the valve presents no obstructions for impeding the flow of blood, thus reducing the risks of thrombosis.

The opening in two phases (proto opening and total opening) by transfer of the axis of rotation of the flap advantageously makes it possible to obtain a progressive increase of the flow of blood.

In order to obtain a flow which is even more laminar, the invention also provides the possibility of making the folded disc of the flap with a concave-convex morphology.

BRIEF DESCRIPTION OF THE DRAWINGS

The invention will be more readily understood on reading the following description accompanied by the attached drawings, in which.

DETAILED DESCRIPTION OF THE PREFERRED EMBODIMENTS

Figure 1:
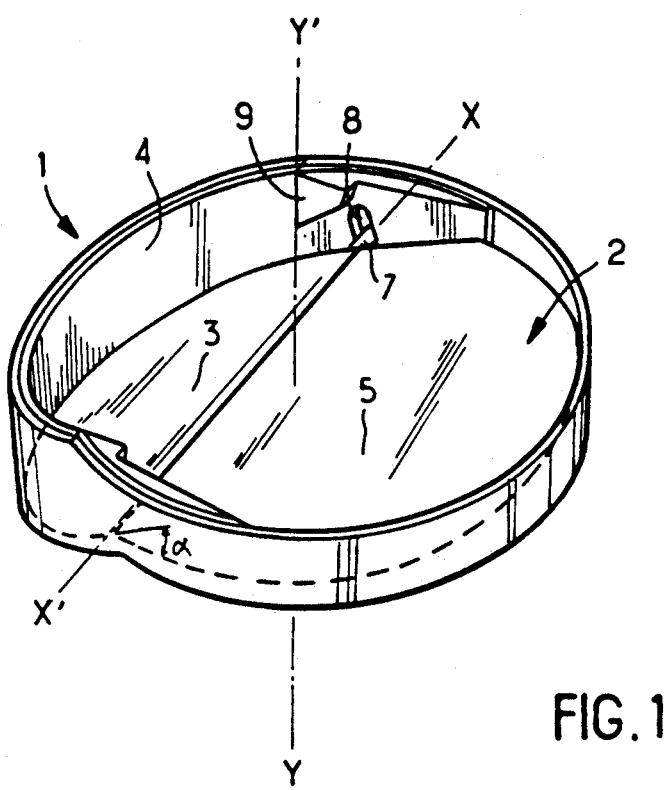
FIG. 1 is a view in perspective of the valve of the invention.
Figure 2:
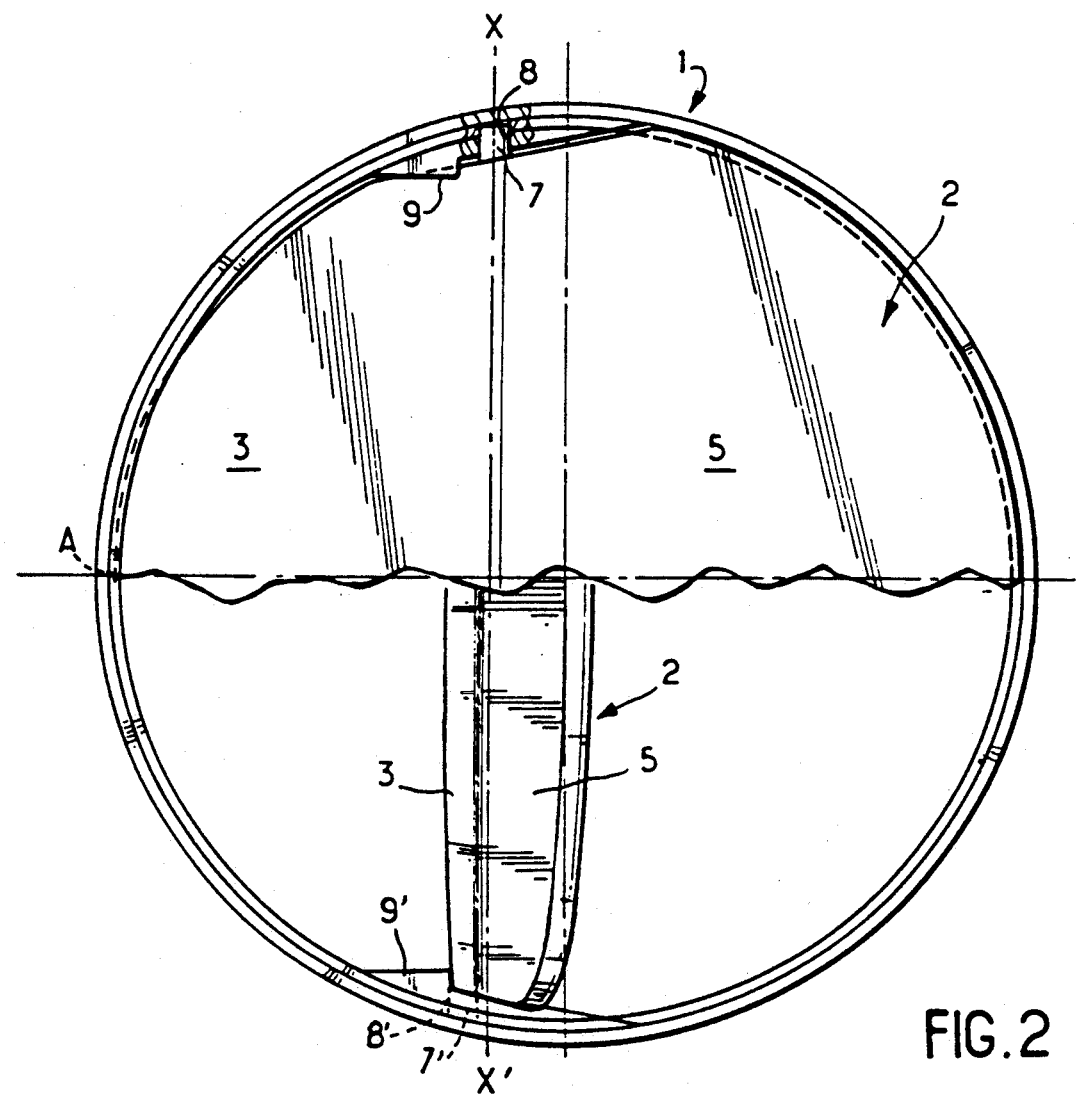
FIG. 2 is a plan view of the valve of the invention in closed (upper half-view) and opened positions lower half-view).

FIGS. 1 and 2 show the valve of the invention respectively in perspective and in plan view, with the element 1 and the flap 2 constituted by a folded disc. Element 1 has a shape which substantially follows the section of flap 2. The lower half-view of FIG. 2 shows flap 2 in position of opening whilst the upper half-view shows it in position of closure.

The disc is folded along an axis XX' parallel to one of its diameters. Axis XX' preferably passes very close to the centre of the disc but may also merge with a diameter. Folding of the disc is such that the latter presents a so-called rear part 3 and a so-called front part 5 located on either side of axis XX'; the rear and front parts form therebetween an angle greater than 150° and preferably 170°.

In the Figures, the angle between the plane of one of parts (3, 5) and the extension of the plane of the other is included between 0° and 30° and is preferably 10°.

In the preferred embodiment of the invention as illustrated in the Figures, axis ZZ' constituting the axis of rotation for the second phase of opening merges with axis XX'. However, in another embodiment of the invention, rotation for the second phase of opening may be effected about an axis ZZ' parallel but distinct from the axis of folding XX'.

In the most general case of axes XX' and ZZ' being parallel without merging, the front and rear parts of the flap 2 are defined with respect to axis ZZ'. In that case, the rear part lies between axis ZZ' and point A and the front part beyond axis ZZ'; axis XX' being able to be located equally well on one side or the other of axis ZZ'.

Figure 3:
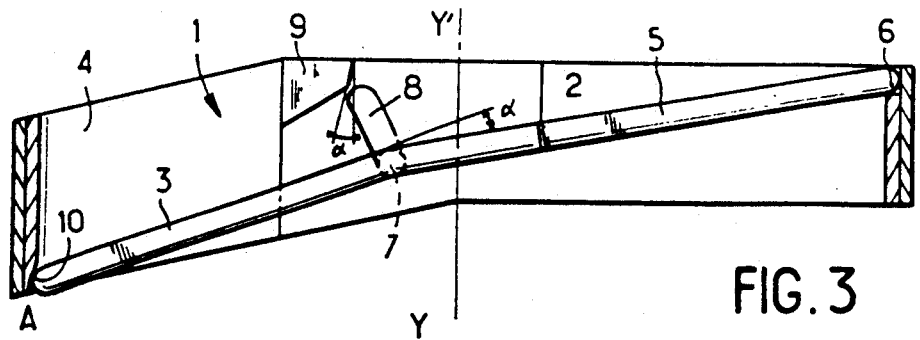
FIGS. 3, 4 and 5 are views in section of the valve of the invention respectively in three different positions of the flap.

FIG. 3 shows the valve in section in the position of closure.

In the position of closure, the rear part 3 of the flap 2 is in contact at point A with the lower edge of the side wall 4 of the element 1.

The contact point A performs the role of a hinge during the first phase of opening. The side wall 4, whilst having a section following that of the flap 2, nonetheless presents a partial cut-out 10 in its lower edge, forming a stop at the level of the contact and hinging point A with the rear part 3 of the flap 2.

Still in position of closure, the front part 5 of flap 2 rests on a seat 6 made on the upper edge of the internal side wall of element 1.

The linking elements of the flap 2 with the element 1 are constituted by two symmetrical lateral pivots (7, 7') provided on axis ZZ' here merged with axis XX' and on each side of flap 2. These pivots (7, 7') cooperate with guiding and (restraining) means made on the internal lateral wall of the element 1 and which are preferably constituted by two symmetrical lateral slideways (8, 8') made in the mass of the body and corresponding to an arc of circle of centre A and of radius equal to the rear part. Pivots (7, 7') may slide freely and rotate in the slideways (8, 8') during the phases of opening of flap 2.

Element 1 also presents on its internal lateral wall at the level of the upper end of the slideways (8, 8'), two stops (9, 9') adapted to limit and orient rotation of flap 2 during opening.

Figure 4:
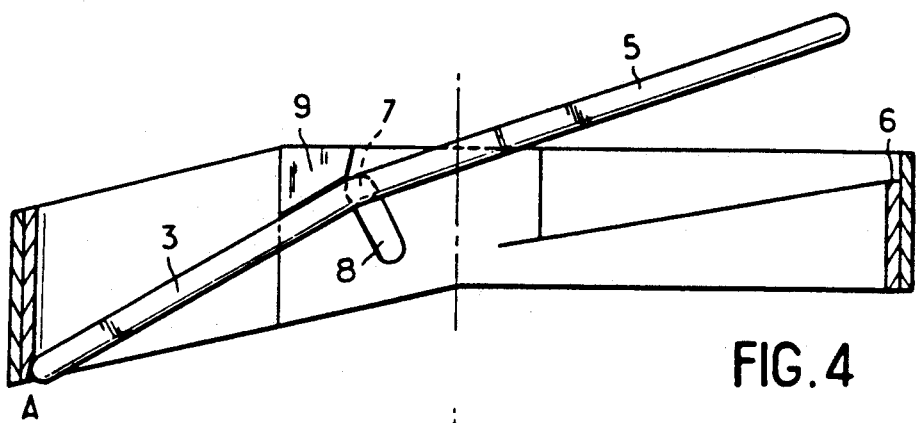

FIG. 4 shows the valve in section during the first phase of opening, also called proto-opening.

This phase corresponds to a rotation of the flap 2 through some degrees about the contact and hinging point A of the rear part 3 of flap 2 with the lower edge of the lateral wall 4 until pivots (7, 7') abut in the upper part of the slideways (8, 8'). The length of the arc of slideways (7, 7') determines the angle of the rotation.

During the whole of the first phase, the ear part 3 of flap 2 is in pivoting contact about point A. This first phase therefore corresponds to a true rotation and not to a translation. At the end of this first phase, the front part 5 of flap 2 is raised with respect to its seat 6, leaving a passage free for the flow of blood.

Figure 5:
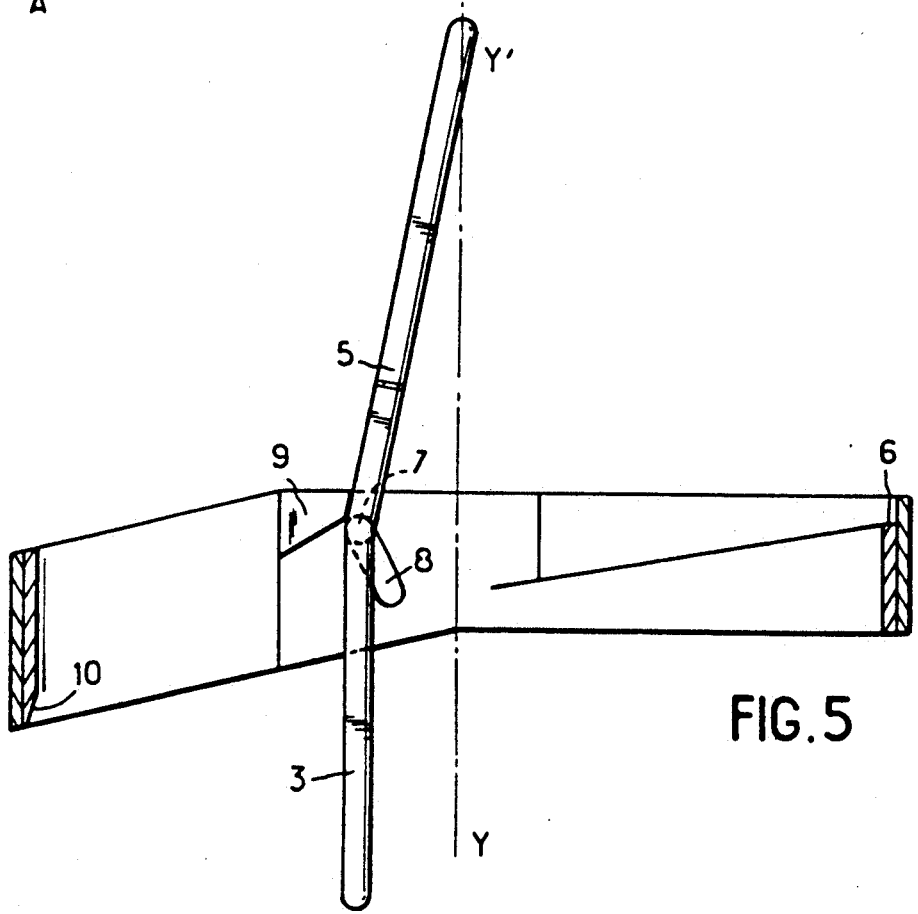

FIG. 5 shows the valve in section in the position of complete opening.

At the end of the first phase of opening, pivots (7, 7') abut in slideways (8, 8') and the rear part 3 abuts against the lower faces of the stops (9, 9') located at the level of the upper end of the slideways (8, 8'). As the flap still has some degrees of freedom, there is produced a transfer of the centre of rotation from point A to axis ZZ' here merged with XX'. At that moment, flap 2 pivots about axis ZZ' (here XX') until the rear part 3 is parallel to axis YY' of the element 1, this corresponding for an angle $\alpha$ of about 10° to a rotation of about 60°.

At the end of this rotation, flap 2 is blocked in abutment on the lateral faces of the stops (9, 9'). These faces are inclined by an angle $\alpha$ with respect to axis YY'. In the final position, the front part 5 therefore makes an angle of about 10° with axis YY'.

In this embodiment, as axis XX' does not pass through the centre of the disc, the rear part 3 is slightly smaller (shorter) than the front part 5.

Of course, as the opening is fairly rapid the two consecutive phases are very short and in any case shorter than the phases of opening of the valves of the prior art, since the angular stroke is less.

Element 1 presents on its external lateral wall means for connection, for example suturing (not shown) with the patient's natural organs.

Figure 6:
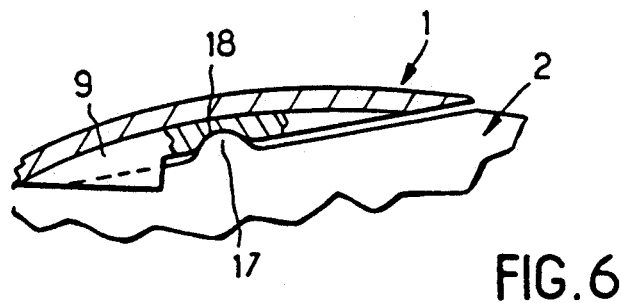
FIG. 6 is a partial plan view of another embodiment of the valve of the invention.

FIG. 6 is a partial plan view of another embodiment of the invention in which the linking elements of flap 2 are constituted by ears or beads (17, 17') forming ball joints and made in the mass of flap 2 adapted to cooperate with guiding and restraining mean constituted by two symmetrical slideways (18, 18') made in the internal lateral wall of element 1.

This embodiment therefore presents more rounded contours than the previous embodiment, this reducing even more the risks of thrombosis and improving the flow of blood. Moreover, positioning of the flap in the element of the valve is facilitated thereby.

Figure 7:
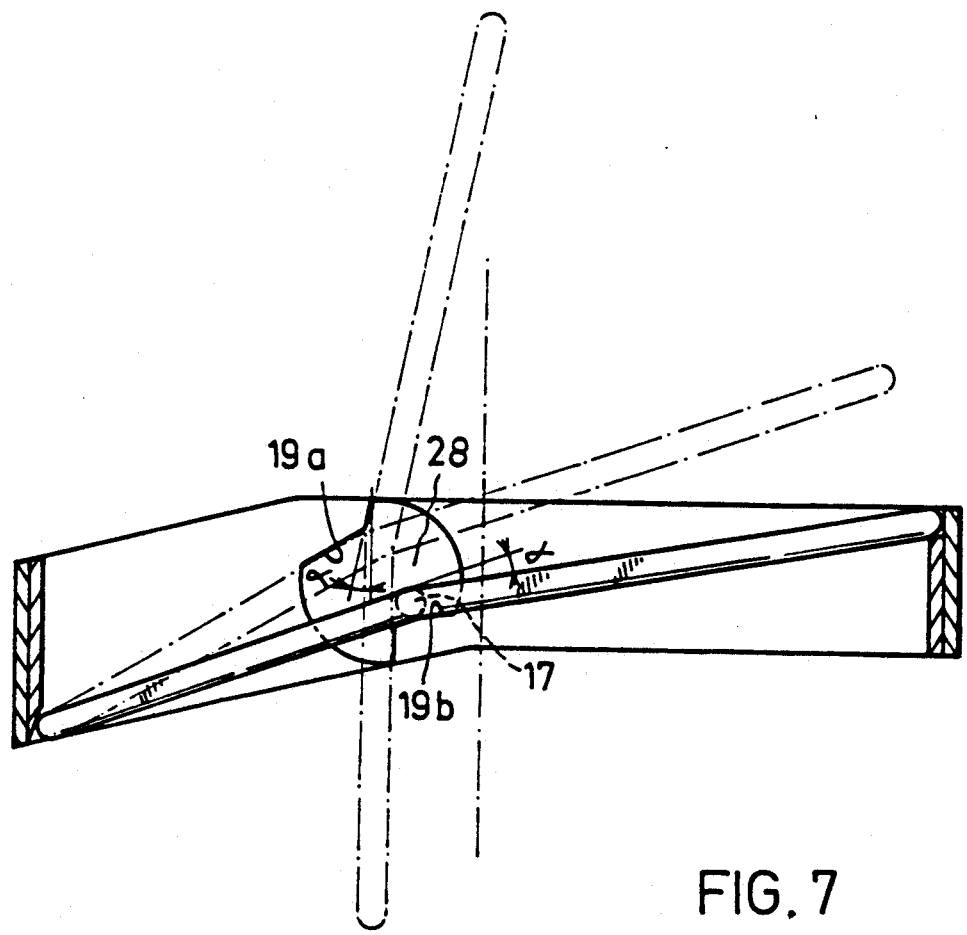
FIG. 7 is a view in section of an embodiment inspired from that of FIG. 6.

FIG. 7 shows a view in section of an embodiment of the valve of the invention in which the linking elements of flap 2 are identical to those described with reference to FIG. 6.

These linking elements cooperate with guiding and restraining means constituted by two symmetrical lateral slideways in cavity form (28, 28') made in the mass of the internal lateral wall of element 1. These cavities (28, 28') comprise over at least a part of their periphery, straight flanks (19a, 19b-19'a, 19'b) forming stops and whose role is also to limit and orient the stroke of flap 2 during opening.

The combination of the cavities (28, 28') and ears (17, 17') corresponds to an articulation of the ball-joint type.

In this embodiment, with the straight flanks (19a, 19b), the stops become unnecessary and are therefore eliminated.

The three positions of flap 2 are shown in FIG. 7.

The orientations of the straight flanks (19a, 19b) with respect to axis YY' are chosen so that the rotation of flap 2 is effected in accordance with what has been described hereinbefore; i.e. the position of complete opening is obtained when the rear part 3 of flap 2 is parallel to axis YY'.

The valve of the invention may be made of any biocompatible material, for example carbon pyrolite or ceramics.

In addition, the flat folded disc may be replaced by a folded disc with concave/convex morphology or with any combination between flat, concave and convex surfaces.

I claim:

1. An artificial cardiac valve made of biocompatible material, comprising:
    an annular valve body having a longitudinal axis, said valve body having guiding and restraining means on an internal sidewall thereof,
    a flap pivotally mounted inside said valve body and having mounting ears cooperable with said guiding and restraining means, wherein said flap comprises a disc folded along a transverse line parallel to a diameter thereof to define a rear part and a front part respectively located on opposite sides of the transverse line, the rear and front parts forming therebetween an angle greater than 150°, and wherein the opening of the valve is effected in two consecutive phases, a first phase corresponding to a rotation of the flap about a contact and hinging point between the rear part of the flap and a lower edge of the internal side wall of said valve body until said mounting ears abut one end of the guiding and restraining means, and a second phase corresponding to a rotation about an axis parallel to said transverse line until the rear part of the flap is parallel to the longitudinal axis of the valve body, wherein said guiding and restraining means comprise two symmetrical lateral guideways in the annular valve body and in which the mounting ears of the flap are movably engaged, said symmetrical lateral guideways corresponding to an arc of a circle having a center at said contact and hinging point and a radius equal to a radius of the rear part of the flap.

2. Cardiac valve according to claim 1 characterized in that said angle is about 170°.

3. Cardiac valve according to claim 1, wherein said mounting ears of the flap comprise two symmetrical lateral pivots provided on said parallel axis.

4. Cardiac valve according to claim 1, wherein said valve body defines two stops for limiting and orienting the two phases of rotation of the flap, and disposed on an internal lateral wall thereof at a level of an upper end of said symmetrical lateral guideways.

5. Cardiac valve according to claim 1, wherein said mounting ears of the flap comprise two lateral ears forming ball-joints, provided on said parallel axis and integral with the flap.

6. Cardiac valve according to claim 1, wherein a lateral wall of said annular valve body has a shape which substantially follows a section of the flap and defines a partial cut-out in a lower edge forming a stop at a level of the contact and hinging point for the rear part of the flap.

7. Cardiac valve according to claim 1, wherein said valve body defines a seat on an upper edge of an internal lateral wall to accommodate an outer edge of the front part of the flap in a position of closure.

8. Cardiac valve according to any one of the preceding claims, wherein surfaces of the flap define a concave or convex morphology.

* * * * *